United States Patent [19]

Gaertner

[11] 4,197,254

[45] Apr. 8, 1980

[54] DERIVATIVES OF N-PHOSPHONOMETHYLGLYCINE

[75] Inventor: Van R. Gaertner, Ballwin, Mo.

[73] Assignee: Monsanto Company, St. Louis, Mo.

[21] Appl. No.: 682,243

[22] Filed: May 3, 1976

[51] Int. Cl.$^2$ .................... C07F 9/30; A01N 9/36
[52] U.S. Cl. .................... 260/502.5; 71/86;
260/326.2; 326/.46; 560/20; 560/123;
560/125; 560/171; 546/22; 549/6
[58] Field of Search .............. 260/502.5, 534 R;
71/86; 560/20, 123, 125, 171

[56] References Cited

U.S. PATENT DOCUMENTS

| | | | |
|---|---|---|---|
| 2,191,738 | 2/1940 | Balle | 260/534 R |
| 2,723,991 | 11/1955 | Sears et al. | 260/518 R |
| 3,324,033 | 6/1967 | Knapp | 260/485 J |
| 3,455,675 | 7/1969 | Irani | 260/502.5 |
| 3,799,758 | 3/1974 | Franz | 260/502.5 |
| 3,816,517 | 6/1974 | Krueger et al. | 260/502.5 |
| 3,853,530 | 12/1974 | Franz | 260/502.5 |
| 3,868,407 | 2/1975 | Franz et al. | 71/86 |
| 3,888,915 | 6/1975 | Alt | 260/501.12 |
| 3,910,969 | 10/1975 | Franz | 71/87 |
| 3,933,946 | 1/1976 | Gaertner | 260/944 |

*Primary Examiner*—Joseph E. Evans
*Attorney, Agent, or Firm*—Arnold H. Cole; Donald W. Peterson

[57] ABSTRACT

A new class of compounds, prepared by reacting a salt of N-phosphonomethylglycine with a cyclic anhydride, have utility as post-emergent herbicides.

16 Claims, No Drawings

DERIVATIVES OF N-PHOSPHONOMETHYLGLYCINE

This invention relates to a novel class of organic chemical compounds. More particularly, the invention is concerned with novel derivatives of N-phosphonomethylglycine obtained by reacting a salt of the glycine with a cyclic anhydride. This class of compounds have been found to be useful as post-emergent herbicides.

U.S. Pat. Nos. 3,799,758 and 3,868,407 describe the use of N-phosphonomethylglycine, and certain esters, amides and salts thereof, as phytotoxicants or herbicides to destroy undesirable plants. A very similar class of compounds, also including certain simple N-acyl derivatives, is described in U.S. Pat. No. 3,853,530 as useful for the non-lethal regulation of the natural growth or development of desirable plants such as crops. In addition, U.S. Pat. Nos. 3,888,915, 3,910,969 and 3,933,946 describe various other N-substituted derivatives of N-phosphonomethylglycine for either or both of the above-mentioned uses. The particular substituents described are nitroso, phenylsulfonamido and hydroxy, respectively.

The novel compounds of the present invention can be illustrated by the formula

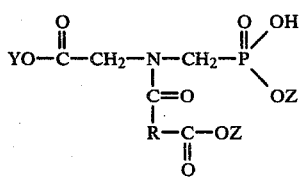

wherein Y is selected from hydrogen, lower alkyl and alkali metal, each Z is selected from hydrogen and alkali metal, and R is selected from vinylene, methylvinylene, alkylene having a chain length of 2 to 3 carbon atoms between the free valences and a total of up to 8 carbon atoms, the monochloro derivatives of such vinylene and alkylene, phenylene, carboxyphenylene, 3-nitrophenylene, tolylene, cyclohexenylene methylcyclohexenylene, cycloalkylene of 4 to 6 carbon atoms, dicarboxycycloalkylene of 4 to 6 ring carbon atoms, dicarboxybenzoylphenylene, norbornenylene, norbornylidene, N-methylpyrrolylidene, pyridylidene, picolylidene and thienylidene, provided that the free valences on the cyclic radicals must be in ortho relationship with respect to the ring carbon atoms. As employed herein, the term "lower alkyl" connotes the straight and branched chain aliphatic hydrocarbon radicals of from 1 to 4 carbon atoms.

Within the genus of the above formula, preferred compounds for purposes of this invention are those wherein R is phenylene, cyclohexenylene or alkylene having a chain length of 2 to 3 carbon atoms between the free valences and a total of up to 5 carbon atoms.

As will be described below, one of the reactants employed in preparing these novel compounds is a cyclic anhydride. It should be recognized that R in the above formula represents the central core of such an anhydride if the

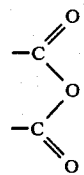

group is removed. The alkylene radicals represented by R are those wherein the chain is obtained from succinic or glutaric anhydride, and they include the substituted chains such as those from 3,3-dimethylglutaric, 2,4-diethylglutaric and 2,2-dipropylsuccinic anhydrides. The cyclic radicals represented by R are those wherein the ring is obtained from anhydrides such as phthalic, the isomeric tetrahydrophthalics, tri- and hemi- mellitic, pyridine-, thiophene- and norbornanedicarboxylic, the cycloalkane dicarboxylics and the like. In the specific case where R represents tolylene, it should be understood that this includes the rings obtained from the isomeric methylphthalic anhydrides and also from homophthalic anhydride (the α, 2-tolylene radical).

It should also be recognized that the cyclic anhydrides which are employed as reactants herein include certain dianhydrides such as benzophenone tetracarboxylic dianhydride and the cycloaliphatic tetracarboxylic dianhydrides. As illustrated in certain of the examples below, reaction takes place across one of the anhydride groups while the second anhydride group is opened to produce ortho dicarboxy substituents.

The novel compounds of the present invention are prepared by condensing the appropriate cyclic anhydride with a di(alkali metal) salt of N-phosphonomethylglycine or with a mono(alkali metal) salt of a lower alkyl glycinate. Said salts are obtained by adding alkali metal hydroxide to the N-phosphonomethylglycine or glycinate in the conventional manner, it being understood that the product of such addition will contain a hydroxyl group attached to the phosphorus atom. The anhydride and the salt can be employed in about equimolar quantities, although it is preferred to employ an excess of said anhydride to assist in completion of the reaction.

This reaction is generally conducted at about room temperature, and cooling means can be used if exothermic increases occur. During this reaction the pH should be in the range of about 6 to 10, preferably about 7 to 9, and this pH range can be readily maintained by periodic additions of alkali as needed.

The product of this reaction is a tri-salt of the formula above (wherein Y and each Z are alkali metal) or a glycinate di-salt (wherein Y is lower alkyl and each Z is alkali metal). As hereinafter described, said product can be used in this form, without isolation or purification, or it can be acidified to remove the alkali metal. Acidification or the reaction product may be accomplished in some cases by treatment with HCl although this procedure can cause partial or complete reversal of the reaction. It is much preferred, therefore, to acidify the salt product via ion exchange chromatography using an ion exchange resin in the acid form.

The following illustrative, non-limiting examples will further demonstrate to those skilled in the art the manner in which specific compounds of this invention can be prepared.

EXAMPLE I

A slurry of 16.9 grams (0.10 mole) of N-phosphonomethylglycine in 30 ml. of water is treated at once with 16 grams (0.20 mole) of 50% aqueous sodium hydroxide. This solution is stirred and cooled to 5°-15° C. to yield the disodium salt of said glycine. An 18.5 gram (0.125 mole) portion of phthalic anhydride, ground to a fine powder in a mortar, is added to the salt solution with vigorous stirring at 20°-25° C. Periodically, 50% aqueous sodium hydroxide is added to maintain a pH of about 6. After stirring overnight, an additional 2.9 grams of phthalic anhydride is added, along with sodium hydroxide to maintain a pH of about 8. The reaction mixture is concentrated below 60° C. and dried to give a brittle foamed glass. A 10 gram portion of the product in 40 ml. of water is then passed through a column of Dowex 50 ion exchange resin in the acid form, and 50 ml. cuts are collected. The second cut is dried twice to yield N-carboxymethyl-N-(phosphonomethyl)phthalamic acid as a colorless glass. Elemental analysis gives 40.97% carbon, 4.25% hydrogen and 9.34% phosphorus as against calculated values of 41.65%, 3.81% and 9.77% for $C_{11}H_{12}NO_8P$.

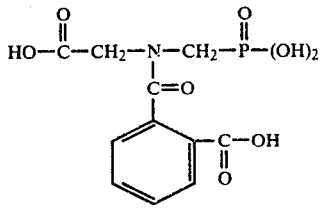

EXAMPLE II

A solution of the disodium salt of N-phosphonomethylglycine is prepared as described in Example I and 11.0 grams (0.11 mole) of finely ground maleic anhydride is added with stirring. Some sodium hydroxide is added to keep the pH at almost 9, and a small portion of ether is added to help dissolve particles of the anhydride. Stirring is continued for several days, and 2.0 or 4.0 gram portions of maleic anhydride are added until no further N-phosphonomethylglycine remains in the reaction mixture. During this period, small portions of sodium hydroxide are added as needed to maintain a pH of about 8. When reaction is complete, the mixture is filtered, rinsed with water, concentrated and then dried. The product, containing disodium maleate by-product, is obtained as a colorless glass, and it is identified by nuclear magnetic resonance (nmr) as the trisodium salt of N-carboxymethyl-N-(phosphonomethyl)maleamic acid.

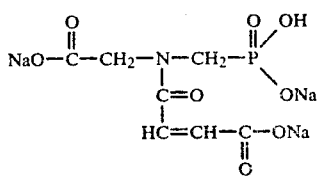

EXAMPLE III

The disodium salt of N-phosphonomethylglycine is prepared as described in Example I using 8.5 grams of the glycine in 15 ml. of water and about 8.1 grams of the sodium hydroxide. The salt solution is cooled and stirred while 5.5 grams of succinic anhydride is added in portions over a period of about 2 hours. Additional sodium hydroxide is added periodically to maintain pH in the desired range, and stirring is continued overnight. The reaction mixture is passed through a column of ion exchange resin in the acid form and dried to a colorless gum. This product is dissolved in water and again passed through the column. The first two 50 ml. cuts are dried, redissolved and redried to yield N-carboxymethyl-N-(phosphonomethyl) succinamic acid (in the monohydrate form) as a colorless glass. Elemental analysis gives 29.46% carbon, 4.57% hydrogen and 10.58% phosphorus as against calculated values of 29.28%, 4.91% and 10.79% for $C_7H_{12}NO_8P \cdot H_2O$.

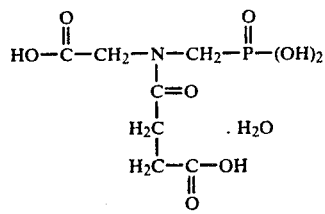

EXAMPLE IV

The disodium salt of N-phosphonomethylglycine is prepared as described in Example III. The salt solution is stirred while 8.5 grams of 3,4,5,6-tetrahydrophthalic anhydride is added, along with sodium hydroxide to maintain the pH above 8. The reaction mixture is rotated overnight, after which a further 1.0 gram of anhydride is added and the reaction mixture stirred to completion. The mixture is filtered to yield a pink solution containing some disodium tetrahydrophthalate as a by-product. The reaction product is identified by nmr as the trisodium salt of N-carboxymethyl-N-phosphonomethyl-3,4,5,6-tetrahydrophthalamic acid.

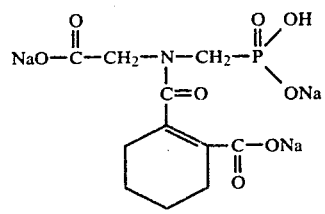

EXAMPLE V

The disodium salt of N-phosphonomethylglycine is prepared as described in Example III. The salt solution is stirred and cooled while 8.5 grams of 1,2,3,6-tetrahydrophthalic anhydride is added in small portions. After rotating overnight, three further 0.5 gram portions of anhydride are added periodically, along with sodium hydroxide to maintain the pH above 8. The reaction mixture is then concentrated, dried, redissolved in water and passed through a column of ion exchange resin in the acid form. The second 50 ml. cut is dried to yield N-carboxymethyl-N-phosphonomethyl-1,2,3,6-tetrahydrophthalamic acid (in the monohydrate form) as a colorless, friable glass. Elemental analysis gives 40.15% carbon, 5.31% hydrogen and 8.94% phosphorus as against calculated values of 38.95%, 5.35% and 9.13% for $C_{11}H_{16}NO_8P \cdot H_2O$.

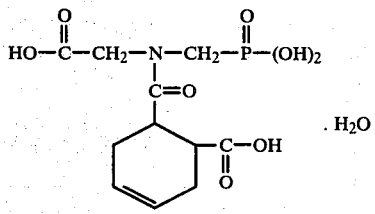

EXAMPLE VI

A solution of about 0.042 moles of the disodium salt of N-phosphonomethylglycine is prepared as described above, and 8.67 grams (0.045 mole) of 3-nitrophthalic anhydride is added with stirring and cooling. Small portions of 50% aqueous sodium hydroxide are added periodically to maintain the pH in the desired range, and 2.0 grams of anhydride is added to complete the reaction. The dried and redissolved reaction mixture is passed through a column of ion exchange resin in the acid form. The second 50 ml. cut is dried twice to yield N-carboxymethyl-N-phosphonomethyl-(3- and 6-nitro)phthalamic acid (in the dihydrate form) as a cream colored brittle glass. The product sinters at 80° C. and shows decomposition at 165° C. Elemental analysis gives 7.10% nitrogen and 7.59% phosphorus as against calculated values of 7.03% and 7.78% for $C_{11}H_{11}N_2O_{10}P \cdot 2H_2O$.

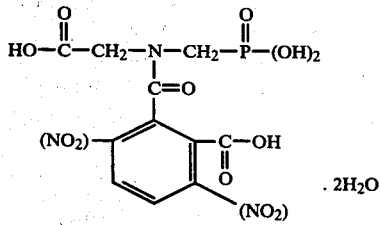

EXAMPLE VII

The disodium salt of N-phosphonomethylglycine is prepared as described in Example III, and 9.0 grams of 5-norbornene-2,3-dicarboxylic anhydride is added with stirring and cooling. After rotating overnight, a further 3.0 gram portion of the anhydride is added, and a final 0.5 gram portion is added several hours later to complete the reaction. During this period, small amounts of sodium hydroxide are added to maintain the pH above 7. The reaction mixture is then filtered to yield a product, containing disodium 5-norbornene-2,3-dicarboxylate as a by-product, as a colorless solution. Said product is identified by nmr as the trisodium salt of N-carboxymethyl-N-phosphonomethyl-5-norbornene-2,3-dicarboxamic acid.

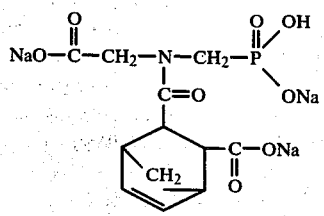

EXAMPLE VIII

The disodium salt of N-phosphonomethylglycine is prepared as described in Example III, and 8.1 grams of homophthalic anhydride is added with stirring. Several small portions of 1.0 or 1.5 grams of anhydride are then added to complete the reaction, and aqueous sodium hydroxide is periodically added to maintain the pH in the desired range. The reaction solution is diluted with water, filtered to remove solids, and then passed through a column of ion exchange resin in the acid form. The first two 50 ml. cuts are dried, redissolved in water and redried to yield N-carboxymethyl-N-(phosphonomethyl)homophthalamic acid as a very light yellow brittle glass which sinters at 80° C. with decomposition at 155° C. Elemental analysis gives 43.49% carbon, 4.22% hydrogen and 8.77% phosphorus as against calculated values of 43.52%, 4.26% and 9.35% for $C_{12}H_{14}NO_8P$.

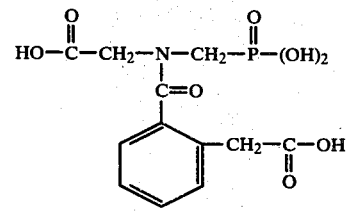

EXAMPLE IX

The disodium salt of N-phosphonomethylglycine is prepared as described in Example III, and 6.3 grams of cyclobutane-1,2-dicarboxylic anhydride is added with stirring. A few drops of aqueous sodium hydroxide is periodically added to maintain the pH at about 8, and a further 0.6 gram portion of anhydride is added to complete the reaction. The reaction mixture is dried and redissolved in water, after which it is passed through a column of ion exchange resin in the acid form. The second 50 ml. cut is dried twice to yield N-carboxymethyl-N-phosphonomethyl-2-carboxycyclobutanecarboxamide as a white, brittle glass which sinters at about 87° C. and shows decomposition at 172° C. Elemental analysis gives 35.64% carbon, 4.69% hydrogen and 10.07% phosphorus as against calculated values of 36.62%, 4.78% and 10.49% for $C_9H_{14}NO_8P$.

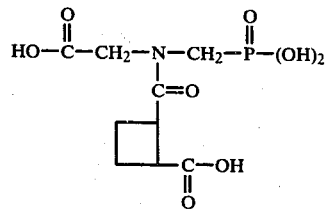

EXAMPLE X

The disodium salt of N-phosphonomethylglycine is prepared as described in Example III, and 6.0 grams of methylsuccinic anhydride is added with stirring. The mixture is cooled, and 50% aqueous sodium hydroxide is added to maintain a pH of about 8. Two further 1.0 gram portions of anhydride are added, along with alkali, to complete the reaction. The pH is then lowered to below 8 with acetic acid, after which the reaction mixture is diluted with water and passed through a column of ion exchange resin in the acid form. The second 50 ml. cut is dried twice to yield N-carboxymethyl-N-phosphonomethyl-2-methylsuccinamic acid (in the monohydrate form) as a foamed glass. Elemental analysis gives 32.77% carbon, 5.10% hydrogen and 9.97% phosphorus as against calculated values of 31.90%, 5.35% and 10.28% for $C_8H_{14}NO_8P \cdot H_2O$.

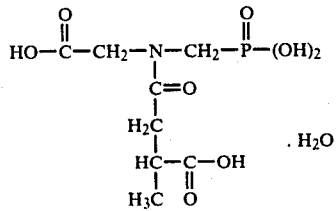

EXAMPLE XI

The disodium salt of N-phosphonomethylglycine is prepared as described in Example III, and 8.5 grams of cyclohexane-1,2-dicarboxylic anhydride is added with stirring. The anhydride dissolves slowly, and sodium hydroxide is added periodically in small amounts to maintain a pH of about 8. A further 1.0 gram portion of the anhydride is added to complete the reaction, and the reaction mixture is filtered to yield a product as a colorless solution, containing disodium cyclohexane-1,2-dicarboxylate as a by-product. Said product is identified by nmr as the trisodium salt of N-carboxymethyl-N-phosphonomethyl-2-carboxycyclohexanecarboxamic acid.

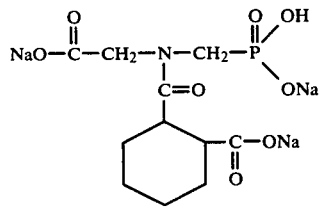

EXAMPLE XII

The disodium salt of N-phosphonomethylglycine is prepared as described in Example III, and 7.8 grams of 2,3-pyridinedicarboxylic anhydride is added with stirring. Two further 2.0 gram portions of the anhydride are added to complete the reaction, and small amounts of 50% aqueous sodium hydroxide are periodically added to maintain the pH in the desired range. The reaction mixture is passed through a column of ion exchange resin in the acid form, and the first several cuts are dried twice to yield N-carboxymethyl-N-(phosphonomethyl)quinolinamic acid (in the monohydrate form) as a friable white solid. Elemental analysis gives 36.23% carbon, 3.89% hydrogen, 8.38% nitrogen and 9.24% phosphorus as against calculated values of 35.73%, 3.90%, 8.33% and 9.21% for $C_{10}H_{11}N_2O_8P \cdot H_2O$.

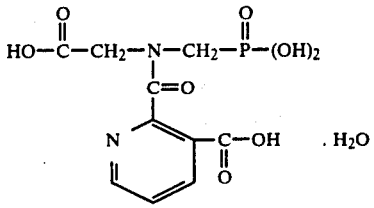

EXAMPLE XIII

A solution of the disodium salt of N-phosphonomethylglycine is prepared as described in Example I except that 0.03 mole of the glycine and 0.06 mole of the hydroxide are employed. To this solution there is added 6.4 grams of trimellitic anhydride with stirring, and small amounts of 50% aqueous sodium hydroxide are added periodically to maintain a pH of 7–9. Further, 1.0 and 2.0 gram portions of the anhydride are added to complete the reaction. A portion of the reaction mixture was passed through a column of ion exchange resin in the acid form, after which several cuts were recombined and made slightly alkaline. An additional 1.0 gram of anhydride, along with alkali, is added to the resultant solution, which is then concentrated and passed through another ion exchange column. The first two 20 ml. cuts are dried twice to yield N-carboxymethyl-N-phosphonomethyl-2,4-dicarboxybenzamide (in the monohydrate form) as a colorless friable glass. Elemental analysis gives 38.30% carbon, 3.26% hydrogen, 3.82% nitrogen and 8.15% phosphorus as against calculated values of 38.00%, 3.72%, 3.69% and 8.16% for $C_{12}H_{12}NO_{10}P \cdot H_2O$.

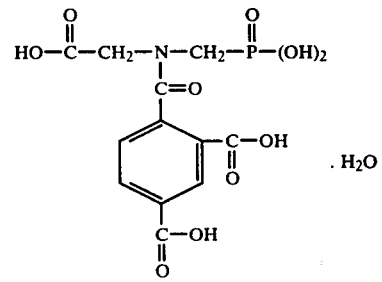

EXAMPLE XIV

A solution of the disodium salt of N-phosphonomethylglycine is prepared as described in Example XIII, and 4.7 grams of 3,3-dimethylglutaric anhydride is added with stirring. Periodic additions of 50% aqueous sodium hydroxide are made to maintain a pH of 8–9, and further 1.5 and 1.0 gram portions of anhydride are added to complete the reaction. The reaction mixture is then passed through a column of an ion exchange resin in the acid form, and the first three 20 ml. cuts are dried to yield N-carboxymethyl-N-phosphonomethyl-3,3-dimethylglutaramic acid as a colorless glass. Elemental analysis gives 39.18% carbon, 6.06% hydrogen, 3.84% nitrogen and 8.38% phosphorus as against calculated values of 38.59%, 5.83%, 4.50% and 9.95% for $C_{10}H_{18}NO_8P$.

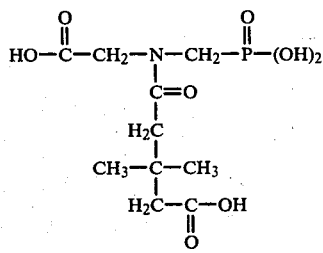

EXAMPLE XV

A solution of the disodium salt of N-phosphonomethylglycine is prepared as described in Example XIII, and 4.7 grams of 2,2-dimethylglutaric anhydride is added with stirring. Periodic additions of small amounts of sodium hydroxide are made to maintain a pH of 8–9, and further 2.0 and 1.5 gram portions of anhydride are added to complete the reaction. The reaction mixture is then passed through a column of ion exchange resin in the acid form. The second and third 20 ml. cuts are combined and dried to yield N-carboxymethyl-N-phosphonomethyl-2,2-dimethylglutaramic acid as an amber glass. Elemental analysis gives 38.81% carbon, 5.91% hydrogen, 4.06% nitrogen and 8.92% phosphorus as against calculated values of 38.59%, 5.83%, 4.50% and 9.95% for $C_{10}H_{18}NO_8P$.

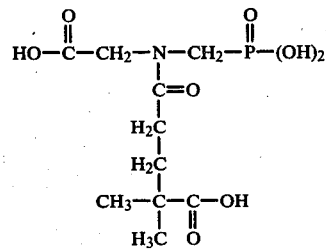

EXAMPLE XVI

A suitable reaction vessel is charged with 3.94 grams (0.02 mole) of ethyl N-phosphonomethylglycinate in 15 ml. of water. While cooling below about 15° C. in an icebath, 50% aqueous sodium hydroxide is added to obtain a pH of about 8. There is then added 2.51 grams (0.022 mole) of methylsuccinic anhydride with stirring and continued cooling. Two further 1.0 gram portions of anhydride are added to complete the reaction, the pH being maintained with additional alkali. The reaction mixture is diluted with water and passed through a column of ion exchange resin in the acid form. The first seven 20 ml. cuts are combined in 20 ml. of water, and a further 1.2 gram portion of anhydride is added. The resultant reaction mixture is passed through the column, and the first four 20 ml. cuts are combined and dried. The product is cooled in dry ice to yield N-carbethoxymethyl-N-(phosphonomethyl)-2-methylsuccinamic acid (in the monohydrate form) as a clear glass-gum. Elemental analysis gives 4.01% nitrogen and 9.13% phosphorus as against calculated values of 4.25% and 9.40% for $C_{10}H_{18}NO_8P \cdot H_2O$.

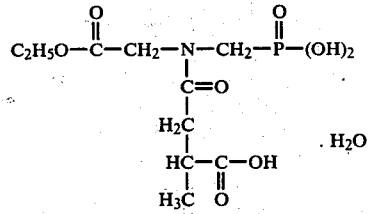

EXAMPLE XVII

Ethyl N-phosphonomethylglycinate in water is cooled and treated with sodium hydroxide as described in Example XVI. There is then added 3.0 grams of 2,3-pyridinedicarboxylic anhydride with stirring. Two further 1.0 gram portions of anhydride are added to complete the reaction, the pH being maintained with additional alkali. The reaction mixture is diluted with water and passed through a column of ion exchange resin in the acid form. The first six 20 ml. cuts are combined and dried to yield N-carbethoxymethyl-N-(phosphonomethyl)-quinolinamic acid as a friable glass. Elemental analysis gives 7.94% nitrogen and 8.93% phosphorus as against calculated values of 8.09% and 8.95% for $C_{12}H_{15}N_2O_8P$.

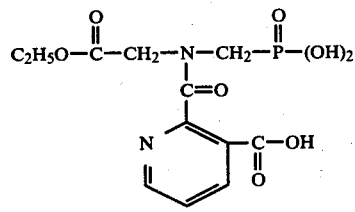

EXAMPLE XVIII

A suitable reaction vessel is charged with 5.47 grams (0.02 mole) of ethyl N-[hydroxy(phenoxy)phosphonomethyl]glycinate in 50 ml. of water, and 50% aqueous sodium hydroxide is added with cooling to obtain a pH just below 8. There is then added 3.3 grams (0.022 mole) of phthalic anhydride in the form of flakes, and the pH level is maintained with small periodic additions of alkali until the reaction is complete. The reaction mixture is diluted with water and passed through a column of ion exchange resin in the acid form. The fourth and fifth 20 ml. cuts are combined, dried to a foam and redried. The product obtained is N-carbethoxymethyl-N-(phosphonomethyl)phthalamic acid as a hygroscopic glass. Elemental analysis gives 43.72% carbon, 4.76% hydrogen and 9.20% phosphorus as against calculated values of 43.25%, 4.84% and 9.29% for $C_{13}H_{16}NO_8P$.

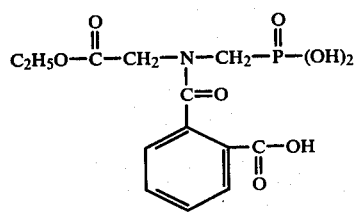

EXAMPLE XIX

To a 28.6 grams (0.03 mole) portion of the disodium salt of N-phosphonomethylglycine, prepared as described in previous examples, there is added 4.2 grams (0.015 mole) of cyclobutane-1,2,3,4-tetracarboxylic dianhydride. A pH of about 8 is maintained with periodic additions of alkali, and further anhydride, in 4.2 grams and 1.0 gram portions, are added to complete the reaction. The reaction mixture is diluted with water and passed through a column of ion exchange resin in the acid form. The second through fourth 20 ml. cuts are collected and dried to yield N-carboxymethyl-N-phosphonomethyl-2,3,4-tricarboxycyclobutanecarboxamide (in the monohydrate form) as a cream colored brittle foam. Elemental analysis gives 33.38% carbon, 3.94% hydrogen, 3.27% nitrogen and 7.31% phosphorus as against calculated values of 32.93%, 4.02%, 3.49% and 7.72% for $C_{11}H_{14}NO_{12}P \cdot H_2O$.

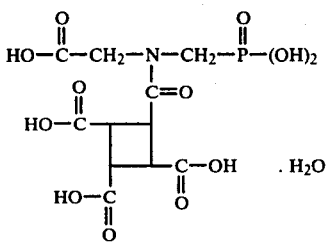

EXAMPLE XX

To a 0.02 mole portion of the disodium salt of N-phosphonomethylglycine, prepared as described in previous examples, there is added 3.2 grams (0.01 mole) of 3,3',4,4'-benzophenonetetracarboxylic dianhydride. A pH of about 8 is maintained with periodic additions of alkali, and further anhydride, in 3.2 grams and 1.0 gram portions, are added to complete the reaction. The reaction mixture is diluted with water and passed through a column of ion exchange resin in the acid form. The second and third 20 ml. cuts are combined and dried to yield 4-(3',4-dicarboxybenzoyl)-N-carboxymethyl-N-(phosphonomethyl)phthalamic acid (in the monohydrate form) as a tan glass. Elemental analysis gives 44.18% carbon, 3.47% hydrogen, 2.77% nitrogen and 6.12% phosphorus as against calculated values of 45.55%, 3.44%, 2.66% and 5.87% for $C_{20}H_{16}NO_{13}P \cdot H_2O$.

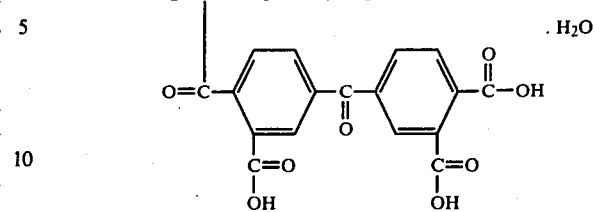

The post-emergence herbicidal activity of various compounds of this invention is demonstrated as follows. The active ingredients are applied in spray form to 14–21 day-old specimens of various plant species. The spray, an aqueous solution containing active ingredient and a surfactant (35 parts butylamine salt of dodecylbenzenesulfonic acid and 65 parts tall oil condensed with ethylene oxide in the ratio of 11 moles ethylene oxide to 1 mole tall oil), is applied to the plants in different sets of pans at several rates (kg per hectare) of active ingredient. The treated plants are placed in a greenhouse and the effects are observed and recorded after approximately 2 weeks or approximately 4 weeks. The data is given in Tables I and II.

The post-emergence herbicidal activity index used in Table I and II is as follows:

| Plant Response | Index |
| --- | --- |
| 0–24% Killed | 0 |
| 25–49% Killed | 1 |
| 50–74% Killed | 2 |
| 75–99% Killed | 3 |
| All Killed | 4 |
| Species Not Present | * |

In said Tables, WAT indicates weeks after treatment, and the plant species treated are each represented by a code letter as follows:

| | |
| --- | --- |
| A | Canada Thistle |
| B | Cocklebur |
| C | Velvet Leaf |
| D | Morning Glory |
| E | Lambsquarter |
| F | Smartweed |
| G | Nutsedge |
| H | Quackgrass |
| I | Johnson Grass |
| J | Downy Brome |
| K | Barnyard Grass |
| L | Soybean |
| M | Sugar Beet |
| N | Wheat |
| O | Rice |
| P | Sorghum |
| Q | Wild Buckwheat |
| R | Hemp Sesbania |
| S | Panicum Spp |
| T | Crabgrass |

TABLE I

| Compound | WAT | Kg h | A | B | C | D | E | F | G | H | I | J | K |
| --- | --- | --- | --- | --- | --- | --- | --- | --- | --- | --- | --- | --- | --- |
| I | 2 | 11.2 | 4 | 3 | 2 | 2 | 4 | 4 | 2 | 4 | 3 | 2 | 3 |
|  | 4 | 11.2 | 4 | 4 | 3 | 2 | 4 | 4 | 3 | 4 | 4 | 2 | 4 |
|  | 2 | 5.6 | 2 | 2 | 2 | 1 | * | 3 | 2 | 3 | 3 | 2 | 4 |
|  | 4 | 5.6 | 2 | 2 | 2 | 1 | * | 3 | 3 | 4 | 3 | 3 | 4 |

TABLE I-continued

| Compound | WAT | Kg h | \multicolumn{11}{c|}{Plant Species} |
| | | | A | B | C | D | E | F | G | H | I | J | K |
|---|---|---|---|---|---|---|---|---|---|---|---|---|---|
| II | 2 | 11.2 | 0 | 0 | 0 | 0 | 4 | 0 | 1 | 0 | 0 | 0 | 0 |
|  | 2 | 5.6 | 0 | 0 | 0 | 0 | 1 | 1 | 0 | 0 | 0 | 0 | 0 |
| III | 2 | 11.2 | 2 | 2 | 3 | 2 | 3 | 2 | 2 | 1 | 3 | 2 | 2 |
|  | 4 | 11.2 | 2 | 2 | 3 | 2 | 2 | 1 | 2 | 2 | 4 | 3 | 2 |
|  | 2 | 5.6 | 2 | 3 | 1 | 2 | 2 | 4 | 2 | 2 | 3 | 2 | 2 |
|  | 4 | 5.6 | 2 | 4 | 1 | 3 | 1 | 4 | 3 | 3 | 4 | 1 | 3 |
| IV | 2 | 11.2 | 2 | 3 | 3 | 2 | 4 | 4 | 1 | 4 | 4 | 3 | 4 |
|  | 4 | 11.2 | 2 | 4 | 3 | 2 | 4 | 4 | 3 | 4 | 4 | 4 | 4 |
|  | 2 | 5.6 | 2 | 3 | 2 | 1 | 4 | 4 | 1 | 4 | 4 | 2 | 3 |
|  | 4 | 5.6 | 2 | 4 | 3 | 2 | 4 | 4 | 3 | 4 | 4 | 3 | 4 |
|  | 2 | 11.2 | 3 | 4 | 3 | 3 | 2 | 4 | 1 | 2 | 3 | 3 | 3 |
|  | 4 | 11.2 | 3 | 4 | 4 | 3 | 3 | 4 | 3 | 3 | 4 | 3 | 3 |
|  | 2 | 5.6 | 3 | 3 | 3 | 2 | 3 | 4 | 1 | 3 | 3 | 2 | 2 |
|  | 4 | 5.6 | 2 | 4 | 3 | 3 | 3 | 4 | 2 | 3 | 3 | 2 | 3 |
| V | 2 | 11.2 | 3 | 4 | 2 | 2 | 4 | 4 | 3 | 4 | 3 | 3 | 4 |
|  | 4 | 11.2 | 4 | 4 | 3 | 2 | 4 | 4 | 3 | 4 | 3 | 4 | 4 |
|  | 2 | 5.6 | 2 | 2 | 1 | 1 | 2 | 4 | * | 1 | 3 | 1 | 3 |
|  | 4 | 5.6 | 2 | 2 | 2 | 2 | 2 | 4 | * | 2 | 4 | 1 | 4 |
| VI | 2 | 11.2 | 3 | 2 | 1 | 1 | 3 | 2 | 3 | 2 | 4 | 2 | 3 |
|  | 4 | 11.2 | 3 | 2 | 1 | 2 | 4 | 2 | 3 | 3 | 4 | 3 | 4 |
|  | 2 | 5.6 | 2 | 2 | 1 | 1 | 2 | 3 | 2 | 1 | 2 | 1 | 2 |
|  | 4 | 5.6 | 2 | 2 | 2 | 2 | 2 | 4 | 2 | 2 | 3 | 1 | 3 |
| VII | 2 | 11.2 | 4 | 4 | 3 | 3 | 4 | 4 | 3 | 4 | * | 2 | 4 |
|  | 4 | 11.2 | 4 | 4 | 4 | 4 | 4 | 4 | 3 | 4 | * | 2 | 4 |
|  | 2 | 5.6 | 4 | 4 | 3 | 2 | 4 | 4 | 2 | 4 | 4 | 3 | 4 |
|  | 4 | 5.6 | 4 | 4 | 3 | 2 | 4 | 4 | 2 | 4 | 4 | 3 | 4 |
|  | 2 | 11.2 | 3 | 4 | 4 | 3 | 2 | 4 | 2 | 3 | 4 | 3 | 3 |
|  | 4 | 11.2 | 4 | 4 | 4 | 4 | 1 | 4 | 3 | 3 | 4 | 3 | 3 |
|  | 2 | 5.6 | 3 | 4 | 3 | 2 | 1 | 4 | 1 | 1 | * | 3 | 2 |
|  | 4 | 5.6 | 4 | 4 | 3 | 2 | 2 | 4 | 2 | 2 | * | 2 | 3 |
| VIII | 2 | 11.2 | 2 | 3 | 1 | 1 | 3 | 4 | 2 | 2 | 3 | 2 | 3 |
|  | 4 | 11.2 | 3 | 3 | 2 | 2 | 4 | 4 | 2 | 3 | 3 | 3 | 3 |
|  | 2 | 5.6 | 3 | 1 | 2 | 1 | 2 | 3 | 1 | 1 | 1 | 1 | 2 |
|  | 4 | 5.6 | 4 | 2 | 1 | 2 | 3 | 3 | 2 | 2 | 1 | 2 | 3 |
| IX | 2 | 11.2 | 4 | 3 | 2 | 1 | 3 | 4 | 2 | 3 | 4 | 2 | 4 |
|  | 4 | 11.2 | 4 | 4 | 3 | 3 | 4 | 4 | 3 | 3 | 4 | 3 | 4 |
|  | 2 | 5.6 | 2 | 2 | 2 | 1 | 1 | 3 | 1 | 2 | 4 | 2 | 3 |
|  | 4 | 5.6 | 2 | 2 | 2 | 2 | 2 | 3 | 2 | 3 | 4 | 3 | 4 |
| X | 2 | 11.2 | 3 | 3 | 3 | 2 | 4 | 3 | 3 | 3 | 3 | 2 | 3 |
|  | 4 | 11.2 | 4 | 4 | 4 | 3 | 4 | 4 | 3 | 4 | 4 | 4 | 4 |
|  | 2 | 5.6 | 3 | 3 | 2 | 2 | 2 | 3 | 2 | 3 | 2 | 2 | 3 |
|  | 4 | 5.6 | 3 | 4 | 3 | 2 | 2 | 4 | 3 | 4 | 4 | 3 | 3 |
| XI | 2 | 11.2 | 1 | 2 | 1 | 1 | 3 | 3 | 3 | 1 | 2 | 1 | 3 |
|  | 4 | 11.2 | 4 | 4 | 1 | 1 | 4 | 4 | 4 | 3 | 2 | 3 | 4 |
|  | 2 | 5.6 | 1 | 1 | 1 | 1 | 2 | 3 | 1 | 1 | 2 | 1 | 3 |
|  | 4 | 5.6 | 2 | 4 | 1 | 1 | 4 | 3 | 2 | 3 | 3 | 3 | 4 |
| XII | 2 | 11.2 | 2 | 2 | 3 | 2 | 3 | 4 | 2 | 2 | 2 | 3 | 3 |
|  | 4 | 11.2 | 3 | 3 | 4 | 3 | 4 | 4 | 2 | 4 | 2 | 4 | 3 |
|  | 2 | 5.6 | 4 | 1 | 1 | 1 | 1 | 4 | 1 | 2 | 1 | 1 | 3 |
|  | 4 | 5.6 | 4 | 2 | 2 | 1 | 2 | 4 | 1 | 1 | 1 | 1 | 4 |
| XIII | 2 | 11.2 | 3 | 4 | 3 | 2 | 4 | 4 | 1 | 3 | 2 | 3 | 3 |
|  | 4 | 11.2 | 4 | 4 | 4 | 2 | 4 | 4 | 2 | 4 | 3 | 4 | 4 |
|  | 2 | 5.6 | 3 | 3 | 3 | 2 | 4 | 4 | 1 | 1 | 1 | 3 | 3 |
|  | 4 | 5.6 | 3 | 3 | 3 | 2 | 4 | 4 | 2 | 1 | 1 | 3 | 3 |
| XIV | 2 | 11.2 | 3 | 2 | 3 | 2 | 3 | 3 | 1 | 3 | 1 | 3 | 3 |
|  | 4 | 11.2 | 4 | 3 | 4 | 2 | 4 | 4 | 2 | 3 | 1 | 3 | 3 |
|  | 2 | 5.6 | 2 | 2 | 2 | 2 | 3 | 3 | 1 | 2 | 0 | 2 | 3 |
|  | 4 | 5.6 | 3 | 3 | 2 | 2 | 4 | 4 | 1 | 2 | 1 | 2 | 3 |
| XV | 2 | 11.2 | 4 | 2 | 3 | 2 | 3 | 3 | 1 | 2 | 0 | 2 | 3 |
|  | 4 | 11.2 | 4 | 2 | 4 | 2 | 3 | 3 | 1 | 2 | 1 | 2 | 3 |
|  | 2 | 5.6 | 1 | 1 | 1 | 1 | 2 | 1 | 1 | 1 | 1 | 1 | 1 |
|  | 4 | 5.6 | 2 | 2 | 1 | 1 | 2 | 1 | 1 | 1 | 1 | 1 | 1 |
| XVI | 2 | 11.2 | 3 | 3 | 3 | 2 | 4 | 4 | 3 | 3 | 3 | 3 | 3 |
|  | 2 | 5.6 | 4 | 3 | 2 | 2 | 4 | 3 | 2 | 3 | 2 | 3 | 3 |
| XVII | 2 | 11.2 | 2 | 2 | 2 | 2 | 2 | 3 | 2 | 3 | 3 | 3 | 3 |
|  | 2 | 5.6 | 1 | 1 | 1 | 1 | 1 | 3 | 1 | 1 | 1 | 2 | 2 |
| XVIII | 2 | 11.2 | 3 | 3 | 2 | 2 | 2 | 4 | 3 | 3 | 3 | 2 | 3 |
|  | 4 | 11.2 | 4 | 3 | 3 | 2 | 4 | 4 | 4 | 4 | 4 | 4 | 4 |
|  | 2 | 5.6 | 3 | 3 | 3 | 2 | 2 | 4 | 3 | 3 | 4 | 3 | 3 |
|  | 4 | 5.6 | 4 | 3 | 4 | 3 | 3 | 4 | 3 | 4 | 4 | 4 | 4 |
| XIX | 2 | 11.2 | 2 | 2 | 1 | 1 | 4 | 4 | 1 | 1 | 1 | 1 | 2 |
|  | 4 | 11.2 | 2 | 2 | 2 | 2 | 4 | 4 | 2 | 1 | 1 | 1 | 2 |
|  | 2 | 5.6 | 1 | 2 | 1 | 1 | 2 | 2 | 1 | 1 | 1 | 0 | 1 |
|  | 4 | 5.6 | 2 | 2 | 1 | 1 | 3 | 3 | 1 | 1 | 1 | 1 | 1 |
| XX | 2 | 11.2 | 3 | 3 | 3 | 2 | 4 | 4 | 3 | 3 | 3 | 3 | 3 |

TABLE II

| Compound | WAT | Kg/h | L | M | N | O | P | B | Q | D | R | E | F | C | J | S | K | T |
|---|---|---|---|---|---|---|---|---|---|---|---|---|---|---|---|---|---|---|
| I | 2 | 5.6 | 3 | 4 | 3 | 3 | 4 | 3 | 4 | 4 | 3 | 4 | 3 | 3 | 4 | 4 | 4 | 4 |
|  | 4 | 5.6 | 3 | 4 | 3 | 4 | 4 | 3 | 4 | 4 | 3 | 4 | 4 | 3 | 4 | 4 | 4 | 4 |
|  | 2 | 1.12 | 1 | 4 | 1 | 1 | 1 | 2 | 1 | 2 | 1 | 2 | 2 | 1 | 3 | 3 | 2 | 4 |
|  | 4 | 1.12 | 1 | 4 | 2 | 1 | 3 | 2 | 2 | 2 | 2 | 3 | 3 | 1 | 3 | 4 | 3 | 4 |
|  | 2 | .28 | 1 | 1 | 1 | 0 | 1 | 1 | 1 | 1 | 1 | 1 | 1 | 1 | 0 | 1 | 2 | 1 |
|  | 4 | .28 | 0 | 1 | 1 | 1 | 1 | 1 | 0 | 1 | 1 | 2 | 1 | 1 | 0 | 2 | 2 | 3 |
|  | 2 | .056 | 0 | 0 | 0 | 0 | 0 | 0 | 1 | 0 | 0 | 0 | 1 | 0 | 1 | 0 | 0 | 2 |
| III | 2 | 5.6 | 3 | 4 | 3 | 3 | 3 | 3 | 3 | 3 | 2 | 4 | 4 | 2 | 3 | 4 | 3 | 3 |
|  | 4 | 5.6 | 3 | 3 | 3 | 3 | 3 | 4 | 4 | 3 | 2 | 4 | 4 | 2 | 3 | 4 | 4 | 4 |
|  | 2 | 1.12 | 1 | 2 | 1 | 1 | 2 | 1 | 1 | 1 | 1 | 1 | 2 | 1 | 2 | 3 | 2 | 3 |
|  | 4 | 1.12 | 0 | 2 | 2 | 1 | 4 | 1 | 2 | 2 | 0 | 1 | 1 | 1 | 2 | 4 | 2 | 3 |
|  | 2 | .28 | 0 | 0 | 1 | 0 | 1 | 1 | 0 | 1 | 0 | 1 | 1 | 0 | 1 | 1 | 1 | 2 |
|  | 4 | .28 | 0 | 0 | 1 | 0 | 1 | 0 | 0 | 1 | 0 | 2 | 1 | 0 | 0 | 2 | 1 | 1 |
| IV | 2 | 5.6 | 1 | 4 | 4 | 3 | 3 | 3 | 2 | 1 | 1 | 4 | 4 | 2 | 4 | 4 | 3 | 4 |
|  | 4 | 5.6 | 1 | 4 | 4 | 3 | 4 | 4 | 3 | 1 | 1 | 4 | 4 | 2 | 4 | 4 | 4 | 4 |
|  | 2 | 1.12 | 0 | 4 | 3 | 1 | 3 | 2 | 1 | 1 | 1 | 4 | 3 | 1 | 2 | 4 | 2 | 4 |
|  | 4 | 1.12 | 0 | 4 | 3 | 3 | 3 | 2 | 2 | 1 | 1 | 4 | 3 | 1 | 3 | 4 | 3 | 4 |
|  | 2 | .28 | 0 | 0 | 0 | 0 | 0 | 0 | 0 | 1 | 0 | 0 | 0 | 0 | 0 | 0 | 1 | 3 |
|  | 2 | .056 | 0 | 0 | 0 | 0 | 0 | 0 | * | 0 | 0 | 1 | 0 | 0 | 0 | 0 | 0 | 1 |
| V | 2 | 5.6 | 3 | 4 | 3 | 4 | 4 | 4 | 4 | 3 | 3 | 4 | 4 | 3 | 4 | 4 | 4 | 4 |
|  | 4 | 5.6 | 3 | 4 | 4 | 4 | 4 | 4 | 4 | 3 | 3 | 4 | 4 | 3 | 4 | 4 | 4 | 4 |
|  | 2 | 1.12 | 1 | 3 | 3 | 1 | 2 | 2 | 2 | 2 | 2 | 4 | 4 | 1 | 2 | 4 | 3 | 4 |
|  | 4 | 1.12 | 1 | 3 | 3 | 1 | 3 | 2 | 0 | 2 | 1 | 4 | 4 | 2 | 2 | 4 | 4 | 4 |
|  | 2 | .28 | 0 | 2 | 2 | 0 | 1 | 1 | 1 | 1 | 1 | 2 | 2 | 1 | 2 | 2 | 2 | 3 |
|  | 4 | .28 | 0 | 2 | 1 | 1 | 2 | 1 | 1 | 2 | 0 | 1 | 4 | 0 | 2 | 4 | 2 | 4 |
| VI | 2 | 5.6 | 2 | 4 | 3 | 4 | 4 | 3 | 3 | 2 | 2 | 4 | 4 | 3 | 3 | 4 | 4 | 4 |
|  | 4 | 5.6 | 3 | 4 | 4 | 4 | 4 | 3 | 4 | 4 | 2 | 4 | 4 | 4 | 4 | 4 | 4 | 4 |
|  | 2 | 1.12 | 1 | 3 | 3 | 1 | 3 | 2 | 2 | 2 | 1 | 4 | 4 | 2 | 2 | 4 | 3 | 4 |
|  | 4 | 1.12 | 1 | 4 | 3 | 1 | 4 | 3 | 2 | 2 | 1 | 4 | 4 | 1 | 4 | 4 | 4 | 4 |
|  | 2 | .28 | 0 | 2 | 0 | 0 | 1 | 2 | 0 | 0 | 0 | 1 | 3 | 0 | 1 | 2 | 1 | 3 |
|  | 4 | .28 | 0 | 4 | 1 | 1 | 2 | 1 | 0 | 1 | 0 | 3 | 3 | 0 | 1 | 3 | 1 | 4 |
|  | 2 | .056 | 0 | 0 | 0 | 0 | 0 | 1 | 0 | 0 | 0 | 0 | 0 | 0 | 0 | 1 | 0 | 0 |
| VII | 2 | 5.6 | 3 | 4 | 4 | 2 | 3 | 3 | 3 | 2 | 1 | 3 | 3 | 3 | 3 | 4 | 3 | 4 |
|  | 4 | 5.6 | 3 | 4 | 4 | 3 | 4 | 4 | 4 | 2 | 1 | 3 | 3 | 3 | 3 | 4 | 4 | 4 |
|  | 2 | 1.12 | 1 | 2 | 2 | 0 | 2 | 2 | 2 | 2 | 1 | 3 | 3 | 2 | 3 | 3 | 2 | 4 |
|  | 4 | 1.12 | 1 | 3 | 3 | 1 | 3 | 2 | 2 | 1 | 1 | 3 | 1 | 3 | 4 | 3 | 4 | 4 |
|  | 2 | .28 | 0 | 1 | 1 | 0 | 1 | 0 | 1 | 1 | 0 | 1 | 1 | 0 | 0 | 1 | 2 | 3 |
|  | 4 | .28 | 0 | 1 | 0 | 0 | 1 | 0 | 0 | 1 | 0 | 0 | 1 | 0 | 0 | 2 | 1 | 3 |
|  | 2 | .056 | 0 | 0 | 1 | 0 | 1 | 0 | 1 | 1 | 0 | 2 | 2 | 1 | 0 | 1 | 1 | 2 |
|  | 4 | .056 | 0 | 0 | 0 | 0 | 1 | 0 | 0 | 1 | 0 | 0 | 2 | 0 | 1 | 3 | 2 | 3 |
| VIII | 2 | 5.6 | 1 | 3 | 4 | 2 | 3 | 2 | 2 | 2 | 1 | 4 | 4 | 3 | 3 | 4 | 3 | 4 |
|  | 4 | 5.6 | 1 | 4 | 4 | 2 | 4 | 3 | 3 | 2 | 1 | 4 | 4 | 4 | 4 | 4 | 4 | 4 |
|  | 2 | 1.12 | 1 | 3 | 3 | 3 | 3 | 2 | 2 | 2 | 1 | 3 | 4 | 1 | 2 | 4 | 2 | 3 |
|  | 4 | 1.12 | 1 | 4 | 3 | 4 | 4 | 2 | 3 | 2 | 1 | 3 | 4 | 1 | 3 | 4 | 3 | 4 |
|  | 2 | .28 | 0 | 0 | 0 | 0 | 1 | 1 | 0 | 0 | 0 | 1 | 3 | 0 | 1 | 0 | 1 | 3 |
|  | 4 | .28 | 0 | 1 | 0 | 0 | 3 | 1 | 0 | 1 | 0 | 3 | 4 | 0 | 1 | 1 | 1 | 3 |
|  | 2 | .056 | 0 | 0 | 0 | 0 | 1 | 0 | 0 | 0 | 0 | 0 | 2 | 0 | 0 | 0 | 0 | 1 |
| IX | 2 | 5.6 | 3 | 4 | 4 | 4 | 4 | 3 | 4 | 3 | 2 | 4 | 4 | 3 | 4 | 4 | 4 | 4 |
|  | 4 | 5.6 | 3 | 4 | 4 | 4 | 4 | 3 | 4 | 4 | 2 | 4 | 4 | 3 | 4 | 4 | 4 | 4 |
|  | 2 | 1.12 | 1 | 3 | 3 | 1 | 2 | 2 | 2 | 2 | 1 | 2 | 3 | 1 | 3 | 4 | 3 | 3 |
|  | 4 | 1.12 | 0 | 4 | 3 | 1 | 4 | 2 | 2 | 2 | 1 | 2 | 3 | 1 | 3 | 4 | 3 | 4 |
|  | 2 | .28 | 0 | 2 | 2 | 1 | 1 | 1 | 1 | 1 | 1 | 1 | 1 | 1 | 3 | 3 | 2 | 3 |
|  | 4 | .28 | 0 | 2 | 1 | 2 | 1 | 1 | 1 | 1 | 0 | 1 | 2 | 0 | 3 | 4 | 2 | 3 |
|  | 2 | .056 | 0 | 0 | 0 | 0 | 0 | 0 | 0 | 0 | 0 | 0 | 0 | 0 | 0 | 0 | 0 | 0 |
| X | 2 | 1.12 | 0 | 4 | 1 | 0 | 0 | 1 | 0 | 1 | 0 | 4 | 4 | 1 | 2 | 4 | 3 | 3 |
|  | 4 | 1.12 | 1 | 4 | 1 | 1 | 2 | 1 | 0 | 1 | 1 | 4 | 4 | 0 | 3 | 4 | 3 | 3 |
|  | 2 | .28 | 2 | 0 | 0 | 0 | 0 | 1 | 0 | 1 | 0 | 4 | 4 | 0 | 1 | 1 | 1 | 3 |
|  | 4 | .28 | 2 | 1 | 0 | 0 | 2 | 1 | 0 | 1 | 0 | 4 | 4 | 0 | 1 | 1 | 1 | 4 |
|  | 2 | .056 | 0 | 0 | 0 | 0 | 0 | 0 | 0 | 0 | 0 | 0 | 0 | 0 | 0 | 0 | 0 | 0 |
| XI | 2 | 5.6 | 1 | 4 | 4 | 1 | 3 | 3 | 4 | 2 | 3 | 4 | 4 | 3 | 3 | 4 | 3 | 4 |
|  | 4 | 5.6 | 1 | 4 | 4 | 1 | 4 | 4 | 4 | 2 | 3 | 4 | 4 | 4 | 3 | 4 | 4 | 4 |
|  | 2 | 1.12 | 0 | 4 | 2 | 0 | 3 | 2 | 2 | 1 | 1 | 2 | 3 | 1 | 2 | 2 | 2 | 3 |
|  | 4 | 1.12 | 0 | 4 | 2 | 0 | 3 | 2 | 2 | 1 | 0 | 4 | 2 | 1 | 4 | 3 | 3 | 3 |
|  | 2 | .28 | 0 | 0 | 0 | 0 | 1 | 0 | 0 | 1 | 0 | 1 | 1 | 0 | 0 | 0 | 1 | 2 |
|  | 4 | .28 | 0 | 1 | 0 | 0 | 1 | 0 | 1 | 0 | 0 | 1 | 0 | 0 | 0 | 0 | 0 | 2 |
|  | 2 | .056 | 0 | 0 | 0 | 0 | 1 | 0 | 0 | 0 | 0 | 0 | 0 | 0 | 1 | 0 | 0 | 1 |
| XII | 2 | 5.6 | 3 | 4 | 4 | 4 | 2 | 3 | 2 | 2 | 4 | 4 | 4 | 2 | 4 | 4 | 4 | 3 |
|  | 4 | 5.6 | 4 | 4 | 4 | 4 | 3 | 4 | 4 | 2 | 4 | 4 | 4 | 3 | 4 | 4 | 4 | 4 |
|  | 2 | 1.12 | 1 | 4 | 2 | 1 | 1 | 1 | 2 | 2 | 4 | 4 | 4 | 3 | 1 | 4 | 2 | 3 |
|  | 4 | 1.12 | 1 | 4 | 2 | 3 | 2 | 2 | 4 | 2 | 4 | 4 | 4 | 3 | 4 | 3 | 3 | 4 |
|  | 2 | .28 | 1 | 1 | 1 | 1 | 1 | 1 | 1 | 1 | 1 | 1 | 1 | 0 | 1 | 1 | 0 | 1 |
|  | 4 | .28 | 1 | 2 | 1 | 1 | 1 | 1 | 1 | 0 | 2 | 2 | 2 | 0 | 0 | 2 | 0 | 0 |
|  | 2 | .056 | 1 | 0 | 1 | 0 | 0 | 0 | 0 | 0 | 0 | 0 | 0 | 0 | 1 | 0 | 0 | 0 |
| XIII | 2 | 5.6 | 3 | 4 | 3 | 4 | 3 | 3 | 2 | 2 | 3 | 4 | 4 | 3 | 3 | 4 | 4 | 4 |
|  | 4 | 5.6 | 3 | 4 | 4 | 4 | 3 | 3 | 3 | 2 | 4 | 4 | 4 | 3 | 4 | 4 | 4 | 4 |
|  | 2 | 1.12 | 1 | 2 | 2 | 2 | 2 | 2 | 1 | 1 | 3 | 3 | 4 | 1 | 1 | 3 | 3 | 3 |
|  | 4 | 1.12 | 1 | 3 | 2 | 2 | 3 | 3 | 1 | 1 | 4 | 3 | 4 | 1 | 1 | 3 | 3 | 3 |
|  | 2 | .28 | 1 | 0 | 1 | 1 | 0 | 0 | 0 | 1 | 1 | 1 | 1 | 0 | 0 | 1 | 1 | 1 |
|  | 4 | .28 | 1 | 0 | 0 | 1 | 0 | 0 | 1 | 1 | 1 | 1 | 1 | 0 | 0 | 1 | 1 | 2 |
|  | 2 | .056 | 1 | 0 | 1 | 0 | 1 | 0 | 0 | 0 | 1 | 0 | 0 | 0 | 0 | 0 | 0 | 1 |

TABLE II-continued

| Compound | WAT | Kg h | L | M | N | O | P | B | Q | D | R | E | F | C | J | S | K | T |
|---|---|---|---|---|---|---|---|---|---|---|---|---|---|---|---|---|---|---|
| XIV | 2 | 5.6 | 2 | 2 | 3 | 3 | 3 | 3 | 3 | 2 | 2 | 4 | 4 | 2 | 2 | 4 | 3 | 4 |
|  | 4 | 5.6 | 3 | 3 | 4 | 4 | 3 | 3 | 3 | 2 | 2 | 4 | 4 | 2 | 3 | 4 | 3 | 4 |
|  | 2 | 1.12 | 1 | 0 | 0 | 0 | 1 | 1 | 1 | 1 | 1 | 1 | 1 | 0 | 1 | 1 | 1 | 2 |
|  | 4 | 1.12 | 1 | 2 | 1 | 1 | 2 | 1 | 1 | 1 | 2 | 2 | 1 | 0 | 1 | 2 | 1 | 2 |
|  | 2 | .28 | 0 | 0 | 1 | 0 | 1 | 0 | 0 | 0 | 0 | 1 | 0 | 0 | 0 | 0 | 0 | 1 |
| XV | 2 | 5.6 | 2 | 1 | 1 | 1 | 2 | 1 | 1 | 1 | 1 | 1 | 1 | 1 | 1 | 1 | 1 | 2 |
|  | 4 | 5.6 | 2 | 2 | 2 | 1 | 3 | 2 | 1 | 1 | 1 | 3 | 1 | 1 | 1 | 1 | 2 | 3 |
|  | 2 | 1.12 | 1 | 1 | 1 | 0 | 1 | 1 | 0 | 1 | 0 | 1 | 0 | 1 | 0 | 1 | 1 | 1 |
|  | 4 | 1.12 | 1 | 1 | 1 | 0 | 1 | 1 | 1 | 1 | 0 | 1 | 0 | 1 | 0 | 1 | 1 | 1 |
|  | 2 | .28 | 0 | 0 | 0 | 0 | 0 | 0 | 0 | 0 | 0 | 0 | 0 | 0 | 0 | 0 | 0 | 0 |
| XVIII | 2 | 1.12 | 1 | 3 | 1 | 1 | 2 | 2 | 3 | 1 | 0 | 4 | 4 | 0 | 1 | 4 | 3 | 4 |
|  | 4 | 1.12 | 1 | 3 | 2 | 2 | 4 | 3 | 3 | 2 | 0 | 4 | 4 | 0 | 4 | 4 | 3 | 4 |
|  | 2 | .28 | 0 | 0 | 1 | 0 | 1 | 1 | 0 | 0 | 0 | 2 | 4 | 0 | 0 | 2 | 1 | 3 |
|  | 4 | .28 | 0 | 1 | 2 | 1 | 2 | 2 | 0 | 1 | 0 | 3 | 4 | 0 | 1 | 2 | 3 | 3 |
|  | 2 | .056 | 0 | 0 | 0 | 0 | 0 | 0 | 0 | 0 | 0 | 2 | 0 | 0 | 1 | 0 | 0 | 0 |
| XIX | 2 | 5.6 | 3 | 4 | 3 | 3 | 3 | 2 | 3 | 2 | 2 | 4 | 3 | 2 | 3 | 3 | 3 | 3 |
|  | 2 | 1.12 | 2 | 2 | 2 | 2 | 2 | 1 | 2 | 2 | 1 | 2 | 2 | 1 | 2 | 2 | 2 | 3 |
|  | 2 | .28 | 1 | 2 | 1 | 1 | 1 | 1 | 0 | 0 | 0 | 1 | 0 | 0 | 0 | 1 | 1 | 1 |

In Table I, the last four lines of data for compound IV and the last four lines of data for compound VII represent the results of tests in which the active ingredient is applied as a simple aqueous solution without the surfactant additive used in all other tests.

From the data presented in the Tables above, it will be apparent that the exemplified compounds of the present invention are effective post-emergent herbicides. However, it should be noted that such data also demonstrate that these compounds display a selectivity of action with respect to the spectrum of plant species employed in the test procedures. Since each of said plant species is selected as a representative of a larger family of plants (e.g., wild buckwheat—Polygonaceae; lambsquarter—Chenopodioceae), those skilled in the art will readily recognize the agronomic crop/weed situations in which this selectivity will be highly desirable.

The phytotoxicant compositions, including concentrates which require dilution prior to application to the plants, of this invention contain at least one active ingredient and an adjuvant in liquid or solid form. The compositions are prepared by admixing the active ingredient with an adjuvant including diluents, extenders, carriers and conditioning agents to provide compositions in the form of finely-divided particulate solids, pellets, solutions, dispersions or emulsions. Thus the active ingredient can be used with an adjuvant such as a finely-divided solid, a liquid of organic origin, water, a wetting agent, a dispersing agent, an emulsifying agent or any suitable combination of these. From the viewpoint of economy and convenience, water is the preferred diluent, particularly where the active ingredient is water soluble.

The phytotoxicant compositions of this invention, particularly liquids, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isethionate, esters of sodium sulfosuccinate, sulfated or sulfonated fatty acid esters, petroleum sulfonates, sulfonated vegetable oils, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl naphthalene sulfonates, sodium naphthalene sulfonate, polymethylene bisnaphthalenesulfonate and sodium N-methyl-N(long chain acid)taurates.

Water-dispersible powder compositions can be made containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The water-dispersible compositions of this invention usually contain from about 5 to about 95 parts by weight of active ingredient, from about 0.25 to 25 parts by weight of wetting agent, from about 0.25 to 25 parts by weight of dispersant and from 4.5 to 94.5 parts by weight of inert extender, all parts being by weight of the total composition. Where required, from about 0.1 to 2.0 parts by weight of the inert extender can be replaced by a corrosion inhibitor or antifoaming agent or both.

Aqueous suspensions can be prepared by mixing together and grinding an aqueous slurry of water-insoluble active ingredient in the presence of dispersing agents to obtain a concentrated slurry of very finely-divided particles. The resulting concentrated aqueous suspension is characterized by its extremely small particle size, so that when diluted and sprayed, coverage is very uniform and usually contains from 5 to about 95 parts by weight active ingredient, from about 0.25 to 25 parts by weight dispersant, and from about 4.5 to 94.5 parts by weight of water.

Emulsifiable oils are usually solutions of active ingredient in water-immiscible or partially water-immiscible solvents together with a surface active agent. Suitable solvents for the active ingredient of this invention include hydrocarbons and water-immiscible ethers, esters or ketones. The emulsifiable oil compositions generally contain from about 5 to 95 parts active ingredient, about 1 to 50 parts surface active agent and about 4 to 94 parts solvent, all parts being by weight based on the total weight of emulsifiable oil.

Although compositions of this invention can also contain other additaments, for example, fertilizers, phytotoxicants and plant growth regulants, pesticides and the like used as adjuvants or in combination with any of the above-described adjuvants, it is preferred to employ the compositions of this invention alone with sequential treatments with the other phytotoxicants, fertilizers and the like for maximum effect. For example, the field could be sprayed with a composition of this invention either before or after being treated with fertilizers, other phytotoxicants and the like. The compositions of this invention can also be admixed with the other materials, e.g. fertilizers, other phytotoxicants, etc., and applied in a single application. Chemicals useful in combination with the active ingredients of this invention either simultaneously or sequentially include for example triazines, ureas, carbamates, acetamides, acetanilides, uracils, acetic acids, phenols, thiolcarbamates, triazoles, benzoic acids, nitriles and the like such as:

3-amino-2,5-dichlorobenzoic acid
3-amino-1,2,4-triazole
2-methoxy-4-ethylamino-6-isopropylamino-s-triazine
2-chloro-4-ethylamino-6-isopropylamino-s-triazine
2-chloro-N,N-diallylacetamide
2-chloroallyl diethyldithiocarbamate
N'-(4-chlorophenoxy)phenyl-N,N-dimethylurea
1,1'-dimethyl-4,4'-bipyridinium dichloride
isopropyl m-(3-chlorophenyl)carbamate
2,2-dichloropropionic acid
S-2,3-dichloroallyl N,N-diisopropylthiolcarbamate
2-methoxy-3,6-dichlorobenzoic acid
2,6-dichlorobenzonitrile
N,N-dimethyl-2,2-diphenylacetamide
6,7-dihydrodipyrido(1,2-a:2',1'-c)-pyrazidiinium salt
3-(3,4-dichlorophenyl)-1,1-dimethylurea
4,6-dinitro-o-sec-butylphenol
2-methyl-4,6-dinitrophenol
ethyl N,N-dipropylthiolcarbamate
2,3,6-trichlorophenylacetic acid
5-bromo-3-isopropyl-6-methyluracil
3-(3,4-dichlorophenyl)-1-methoxy-1-methylurea
2-methyl-4-chlorophenoxyacetic acid
3-(p-chlorophenyl)-1,1-dimethylurea
1-butyl-3-(3,4-dichlorophenyl)-1-methylurea
N-1-naphthylphthalamic acid
1,1'-dimethyl-4,4'-bipyridinium salt
2-chloro-4,6-bis(isopropylamino)-s-triazine
2-chloro-4,6-bis(ethylamino)-s-triazine
2,4-dichlorophenyl-4-nitrophenyl ether
alpha,alpha,alpha-trifluoro-2,6-dinitro-N,N-dipropyl-p-toluidine
S-propyl dipropylthiolcarbamate
2,4-dichlorophenoxyacetic acid
N-isopropyl-2-chloroacetanilide
2',6'-diethyl-N-methoxymethyl-2-chloroacetanilide
monosodium acid methanearsonate
disodium methanearsonate
N-(1,1-dimethylpropynyl)-3,5-dichlorobenzamide Fertilizers useful in combination with the active ingredients include for example ammonium nitrate, urea, potash, and superphosphate.

When operating in accordance with the present invention, effective amounts of the glycines are applied to above-ground portions of plants. The application of liquid and particulate solid herbicidal compositions to above-ground portions of plants can be carried out by conventional methods, e.g. power dusters, boom and hand sprayers and spray dusters. The compositions can also be applied from airplanes as a dust or a spray because of their effectiveness at low dosages. The application of herbicidal compositions to aquatic plants is usually carried out by spraying the compositions on the aquatic plants in the area where control of the aquatic plants is desired.

The application of an effective amount of the compounds of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.25 to about 22.4 or more kilograms per hectare. In applications for control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e. a phytotoxic or herbicidal amount. It is believed that one skilled in the art can readily determine from the teachings of this specification, including examples, the approximate application rate.

Although the invention is described with respect to specific modifications, the details thereof are not to be construed as limitations except to the extent indicated in the following claims.

What is claimed is:

1. A compound of the formula

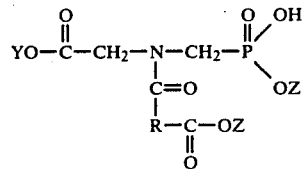

wherein Y is selected from hydrogen, lower alkyl and alkali metal, each Z is selected from hydrogen and alkali metal, and R is selected from vinylene, methylvinylene, alkylene having a chain length of 2 to 3 carbon atoms between the free valences and a total of up to 8 carbon atoms, the monochloro derivatives of such vinylene and alkylene, phenylene, carboxyphenylene, 3-nitrophenylene, tolylene, cyclohexenylene, methylcyclohexenylene, cycloalkylene of 4 to 6 carbon atoms, dicarboxycycloalkylene of 4 to 6 ring carbon atoms, dicarboxybenzoylphenylene, norbornenylene and norbornylidene, provided that the free valences on the cyclic radicals must be in ortho relationship with respect to the ring carbon atoms.

2. A compound as defined in claim 1 wherein R is selected from phenylene, cyclohexenylene and alkylene having a chain length of 2 to 3 carbon atoms between the free valences and a total of up to 5 carbon atoms.

3. A compound as defined in claim 2 wherein Y and Z are alkali metal.

4. A compound as defined in claim 2 wherein Y is lower alkyl.

5. A compound as defined in claim 2 wherein R is phenylene.

6. A compound as defined in claim 2 wherein R is cyclohexenylene.

7. A compound as defined in claim 2 wherein R is alkylene having a chain length of 2 to 3 carbon atoms between the free valences and a total of up to 5 carbon atoms.

8. A compound as defined in claim 1 wherein R is cycloalkylene of 4 to 6 carbon atoms.

9. A compound as defined in claim 1 wherein R is tolylene.

10. A compound as defined in claim 1 where Y and Z are hydrogen.

11. A compound as defined in claim 1 wherein Y is lower alkyl and Z is hydrogen.

12. In a process for preparing a compound of the formula

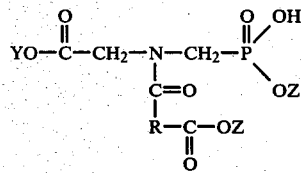

wherein Y is selected from hydrogen, lower alkyl and alkali metal, each Z is selected from hydrogen and alkali metal, and R is selected from vinylene, methylvinylene, alkylene having a chain length of 2 to 3 carbon atoms between the free valences and a total of up to 8 carbon atoms, the monochloro derivatives of such vinylene and alkylene, phenylene, carboxyphenylene, 3-nitrophenylene, tolylene, cyclohexenylene, methylcyclohexenylene, cycloalkylene of 4 to 6 carbon atoms, dicarboxycycloalkylene of 4 to 6 ring carbon atoms, dicarboxybenzoylphenylene, norbornenylene and norbornylidene, provided that the free valences on the cyclic radicals must be in ortho relationship with respect to the ring carbon atoms, the step comprising reacting a di(alkali metal) salt of N-phosphonomethylglycine or a mono(alkali metal) salt of lower alkyl N-phosphonomethylglycinate with an anhydride of the formula

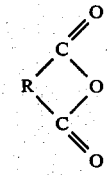

wherein R has the same meaning as above, the pH of the reaction mixture being maintained in the range of about 6 to 10.

13. In a process as defined in claim 12, the further step of employing at least an equimolar amount of the anhydride relative to the glycine.

14. In a process as defined in claim 12, the further step of maintaining the pH of the reaction mixture in the range of about 7 to 9.

15. In a process as defined in claim 14, the further step of employing a molar excess of the anhydride relative to the glycine.

16. In a process as defined in claim 12, the further step of passing the reaction mixture through an ion exchange resin in the acid form.

* * * * *